US012806305B2

(12) United States Patent
Frazier et al.

(10) Patent No.: US 12,806,305 B2
(45) Date of Patent: Nov. 24, 2026

(54) UVC CHAMBER FOR AIR DISINFECTION AND PURIFICATION

(71) Applicants: Ronald Scott Frazier, Boulder City, NV (US); Nicholas A. Connelly, Cary, NC (US)

(72) Inventors: Ronald Scott Frazier, Boulder City, NV (US); Nicholas A. Connelly, Cary, NC (US)

(*) Notice: Subject to any disclaimer, the term of this patent is extended or adjusted under 35 U.S.C. 154(b) by 0 days.

(21) Appl. No.: 19/390,565

(22) Filed: Nov. 15, 2025

(65) Prior Publication Data

US 2026/0137827 A1 May 21, 2026

Related U.S. Application Data

(60) Provisional application No. 63/721,170, filed on Nov. 15, 2024.

(51) Int. Cl.
*A61L 9/20* (2006.01)

(52) U.S. Cl.
CPC ............ *A61L 9/20* (2013.01); *A61L 2209/12* (2013.01)

(58) Field of Classification Search
CPC ........ A61L 9/20; A61L 9/205; A61L 2209/12; A61L 2/088
See application file for complete search history.

(56) References Cited

U.S. PATENT DOCUMENTS 9,540,252 B1* 1/2017 Collins .................... A61L 2/10
2002/0168305 A1* 11/2002 Morrow ................. C01B 13/10 422/186.3
2017/0100494 A1* 4/2017 Dobrinsky .......... A23B 11/164
2017/0224865 A1* 8/2017 Ronda .................... F24F 8/192
2022/0062489 A1* 3/2022 Morgan-Lange ........ B01J 23/31
2022/0062822 A1 3/2022 Dhau et al.
(Continued)

FOREIGN PATENT DOCUMENTS

CN 116808249 A 9/2023
DE 102019125125 A1 3/2021
KR 20220164235 A * 12/2022 ............ A61L 9/205
(Continued)

OTHER PUBLICATIONS

Furman et al., "Influence of the geometry of a monolithic support on the efficiency of photocatalyst for air cleaning", Chemical Engineering Science, vol. 62, pp. 5212-5316, available online Jan. 5, 2007 (Year: 2007).*
(Continued)

*Primary Examiner* — Jennifer Wecker
*Assistant Examiner* — Brady C Pilsbury
(74) *Attorney, Agent, or Firm* — Erickson Law Group, PC

(57) ABSTRACT

An advanced air disinfection and purification system integrating a UVC chamber with TIR lens optics and photocatalytic oxidation using titanium dioxide ($TiO_2$) with PTFE. The UVC chamber is designed to maximize germicidal efficiency through reflective surfaces and focused UVC light. The $TiO_2$ coating on the chamber's interior surfaces generates reactive oxygen species upon exposure to UVC light, effectively degrading pathogens and pollutants. The system is adaptable for integration into existing HVAC systems or as a standalone unit, offering enhanced air quality with minimal maintenance.

17 Claims, 4 Drawing Sheets

(56) References Cited

U.S. PATENT DOCUMENTS

| | | | | |
|---|---|---|---|---|
| 2022/0211897 | A1 * | 7/2022 | Wills, Jr. | A61L 9/205 |
| 2024/0009340 | A1 | 1/2024 | Pau et al. | |

FOREIGN PATENT DOCUMENTS

| | | | | | |
|---|---|---|---|---|---|
| KR | 20230047268 | A | * | 4/2023 | A61L 9/205 |
| WO | WO-02083570 | A1 | * | 10/2002 | A61L 2/088 |
| WO | WO-2022065593 | A1 | * | 3/2022 | A61L 9/205 |
| WO | 2023215164 | A1 | | 11/2023 | |

OTHER PUBLICATIONS

PCT Notification of Transmittal of the International Search Report And The Written Opinion Of The International Searching Authority Or The Declaration, Mar. 19, 2026.

* cited by examiner

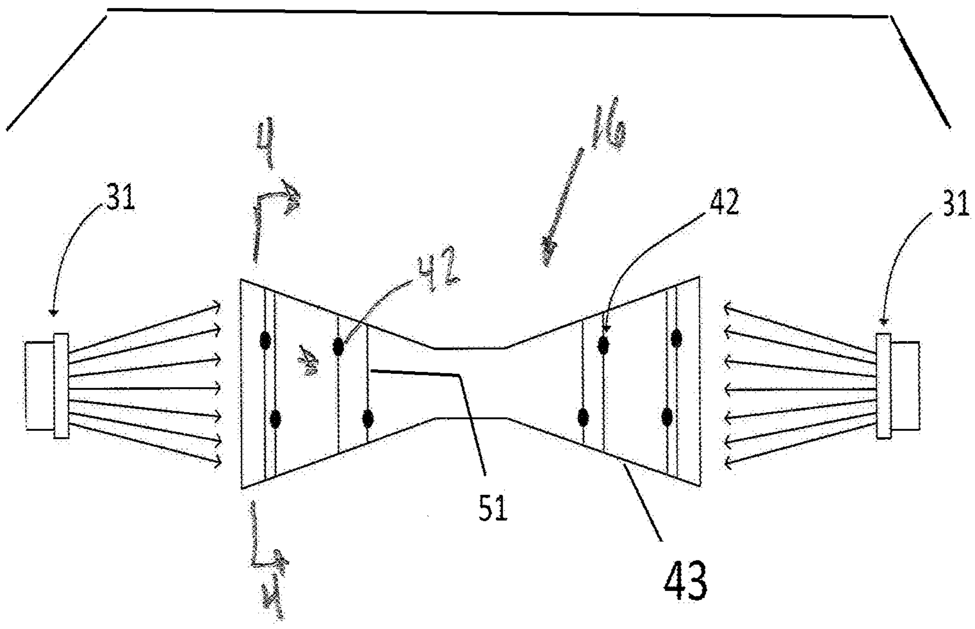
FIG. 2
FIG. 2A
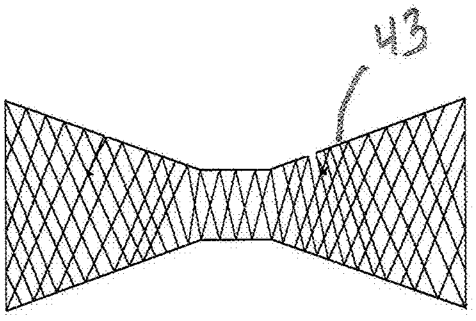

UVC CHAMBER FOR AIR DISINFECTION AND PURIFICATION

The application claims the benefit of U.S. Provisional Application No. 63/721,170 filed Nov. 15, 2024.

BACKGROUND

Existing air purification systems typically rely on filters, UV light, or chemical oxidants to remove contaminants. However, these methods may have limitations in terms of efficiency, maintenance, and the ability to eliminate a broad spectrum of pathogens and pollutants.

SUMMARY

An air disinfection and purification system includes a UVC chamber, wherein the chamber is lined with reflective surfaces and equipped with UVC LEDs emitting at approximately 255 nm-280 nm. Each UVC LED can include a total internal reflection (TIR) lens optic system positioned to direct and focus UVC light within the chamber. The interior of the chamber can include a lattice in the air path coated with a photocatalytic material comprising titanium dioxide ($TiO_2$). Nodes composed of polytetrafluoroethylene (PTFE) further enhance reflectivity of UVC light within the lattice.

This exemplary embodiment of the invention relates to air purification systems, specifically to a system that combines ultraviolet C (UVC) radiation, total internal reflection (TIR) lens optics, and photocatalytic oxidation with titanium dioxide (TiO2) and PTFE to disinfect and purify air.

The embodiment includes an UVC Chamber with TIR Lens Optic, a Titanium Dioxide ($TiO_2$) Photocatalytic Oxidation device, and a PTFE Enhancement device for Air Disinfection and Purification.

The embodiment of the present invention aims to overcome the limitations of the prior art by integrating an UVC chamber with a TIR lens optics, a $TiO_2$-based photocatalytic oxidation device and a PTFE device. The system is designed to maximize disinfection efficiency and air purification while minimizing maintenance requirements and operational costs.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 2 is an exploded schematic diagram of the UVC chamber with TIR lens optics and $TiO_2$ coating with PTFE nodes.

FIG. 2A is a elevational view of a lattice structure portion taken from FIG. 2.

DETAILED DESCRIPTION

Figure 1:
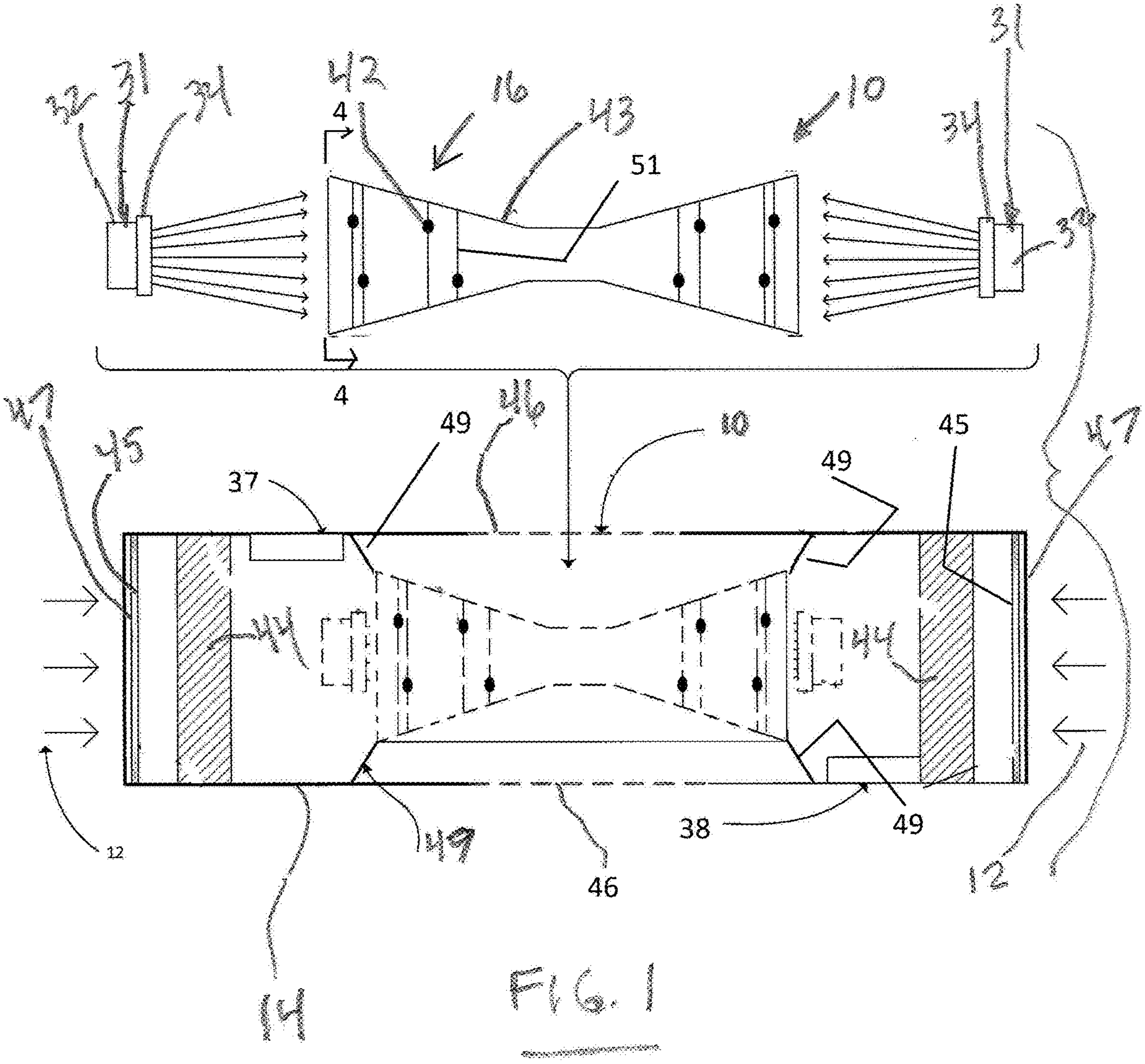
FIG. 1 is an exploded schematic diagram of an exemplary embodiment of a UVC Chamber for Air Disinfection and Purification

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

This application incorporates by reference 63/721,170 filed Nov. 15, 2024 in its entirety.

FIGS. 1 and 2 illustrate an exemplary embodiment of an air disinfection and purification assembly 10.

The assembly includes a housing 14 enclosing a treatment assembly 16. The housing 14 is designed with reflective inner surfaces to ensure maximum UVC light utilization. UVC LED units 31 emitting at a wavelength of approximately 255 nm-280 nm, known for its germicidal properties are included in the treatment assembly 16.

The LEDs units 31 include a UVC LED emitter 32 and a TIR lens optic system 34 positioned to direct and focus UVC light efficiently. The TIR lens optic systems 34 are configured to enhance the intensity of UVC radiation within the chamber, ensuring thorough exposure of air to the germicidal light.

The treatment assembly 16 includes a 3D printed lattice or matrix 43 coated with a thin layer of titanium dioxide ($TiO_2$). The lattice is shown in outline in FIGS. 1 and 2 and shown in more detail in FIG. 2A. The lattice is perforate to pass air therethrough. When exposed to UVC light, $TiO_2$ acts as a photocatalyst, generating reactive oxygen species (ROS) such as hydroxyl radicals and superoxide ions. These ROS effectively degrade organic pollutants and pathogens in the air stream. Nodes, spheres or geometric polygons are suspended within the lattice to enhance reflectivity of UVC light within the lattice.

The system includes an air intake mechanism such as one or more filters 45, one or more fans 44 and one or more air outlets 46 that ensures a controlled flow of air through the UVC housing 14. In the illustrated embodiment, the housing has air inlets 47 at opposite ends and a filter and a fan arranged between the air inlets and the lattice 43. Air is pumped through the lattice 43 through opposite ends thereof and exits the housing through the air outlets 46. The design ensures that the air 12 is exposed to UVC light and the $TiO_2$ surface for an optimal duration to achieve maximum disinfection and purification. Baffles 49 ensures that air entering the housing 14 passes through the chamber 16. If the housing 14 and the lattice structure are cylindrical the baffles 49 can be annular.

The assembly 10 can be integrated into existing HVAC systems or used as a standalone unit. Sensors and control systems monitor the UVC intensity, airflow, and $TiO_2$ surface condition to maintain optimal performance.

The invention includes an innovative 3D-printed lattice structure 43 coated with titanium dioxide ($TiO_2$), which significantly enhances the efficiency of photocatalytic oxidation by maximizing surface area and UV exposure. The lattice structure 43 is carefully designed with interconnected nodes 42 and struts 51, creating a robust and high surface-to-volume ratio matrix that promotes extensive interaction between the air and the photocatalytic surfaces. The lattice structure itself (before coating) can be composed of metal, ceramic, polymer filament, or any other suitable material. It will be dependent on the unit application and environment. A medical application may require a stricter material requirement. Ceramic is the most viable option at this time due to its materials heat properties.

The $TiO_2$ coated lattice structure 43 can be fabricated using high-precision 3D printing techniques, ensuring precise control over pore size, geometry, and overall structural dimensions.

This level of precision allows for the creation of a lattice that facilitates optimal airflow while ensuring thorough exposure to UVC light, thereby enhancing the disinfection and purification processes.

The lattice structure 43 provides a significantly larger surface area compared to traditional flat or randomly coated surfaces, enhancing the photocatalytic reaction efficiency.

The design promotes turbulent airflow within the housing 14, increasing the interaction time between the air and the photocatalytic surfaces, leading to more effective disinfection and pollutant degradation.

The robust design of the lattice structure 43 ensures stability and longevity under continuous UV exposure. Additionally, the modular nature of the structure allows for easy cleaning, maintenance, and replacement, ensuring sustained performance over time.

The 3D-printed $TiO_2$ coated lattice structure 43 can be integrated with additional photocatalytic materials to target a broader spectrum of contaminants. Moreover, the lattice can be treated or doped with specific elements to enhance its photocatalytic activity and durability, making it suitable for various environmental conditions and applications.

The lattice 43 can be in different shapes including a single cone or opposing cones. The smaller end of each cone is folded back into the center and brought back to the front and is then folded back into the cone again. This provides for multiple layers of lattice material. This increases the surface area to a larger value.

These descriptions describe innovative aspects of the 3D-printed $TiO_2$ coated lattice structure, emphasizing its contributions to optimizing air disinfection and purification in the UVC chamber.

To further optimize the performance of the UVC chamber, the 3D-printed $TiO_2$ coated lattice structure 43 incorporates PTFE (Polytetrafluoroethylene) nodes or balls 42. PTFE is chosen for its excellent reflective properties and durability under UVC exposure. These nodes are strategically placed within the lattice to enhance the distribution and intensity of UVC light throughout the structure.

The PTFE nodes 42 are integrated into the $TiO_2$ coated lattice 43 during the 3D printing process, ensuring precise placement and alignment. The nodes are positioned to reflect UVC light onto less directly exposed areas of the $TiO_2$ coated lattice, ensuring a more uniform and intense irradiance. This design maximizes the photocatalytic activity of the $TiO_2$ by ensuring that all surfaces receive sufficient UVC exposure.

This lattice 43 can be dipped into a ceramic slurry and then baked at a low temperature for curing.

For example, the ceramic slurry can be composed of:

- Water;
- Kaolin: 45% kaolin, composed of 25% silica, 10% feldspar, 30% water, 0.3% sodium silicate;
- $TiO_2$: 15 wt % Nanoparticle $TiO_2$;
- Dopants: 0.3 wt % Fe (as $Fe(NO_3)_3$), 1 wt % Ag (as nanoparticles or $AgNO_3$), optional 0.5 wt % Cu (as $Cu(NO_3)_2$); and
- Additives: 0.05 M $H_2O_2$ in reaction medium, optional 0.01 M NaOCl.

This slurry can be refined/can be changed/modified to increase the OH and to tailor to the application.

Use of the slurry can optimize the OH (Hydroxyl radical) by up to 60% from the base $TiO_2$ nanoparticle material.

Nanoparticle $TiO_2$ (titanium dioxide) refers to titanium dioxide particles engineered at the nanoscale, typically with dimensions ranging from 1 to 100 nanometers. These nanoparticles exhibit unique physical, chemical, and optical properties compared to bulk $TiO_2$, due to their high surface area-to-volume, quantum effects, and enhanced reactivity.

Figure 3:
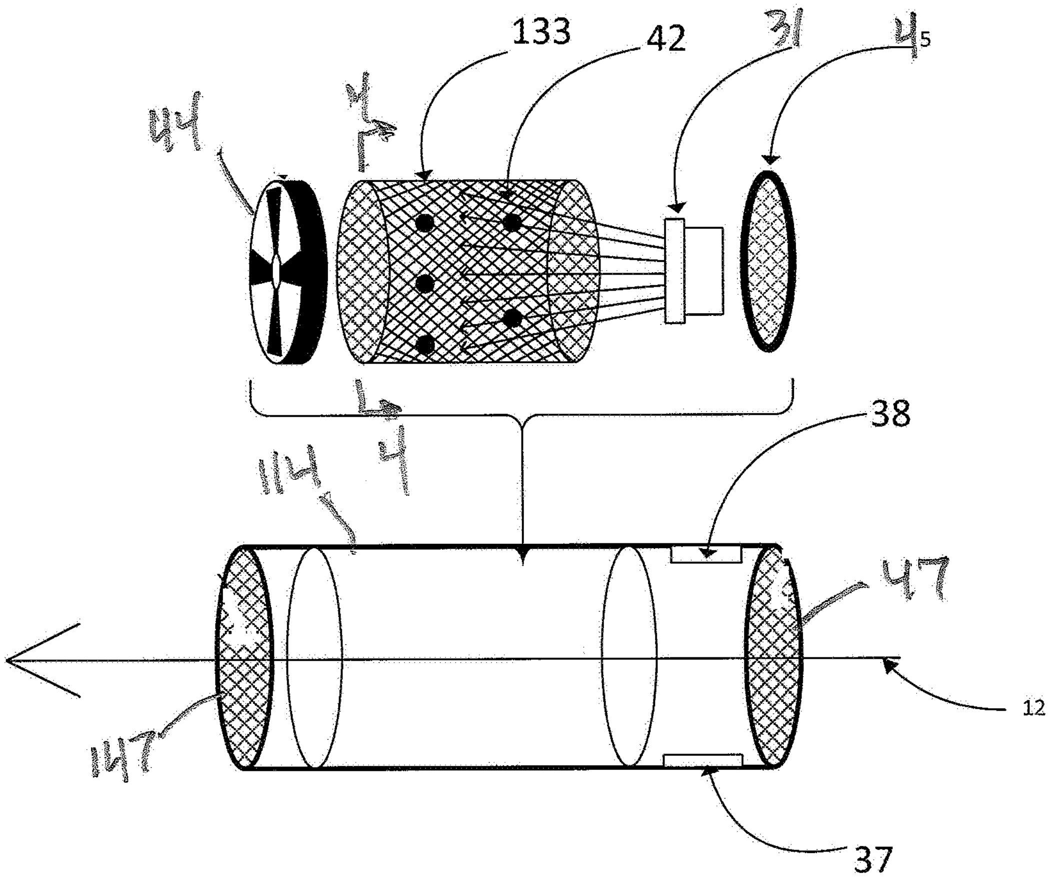
FIG. 3 is an exploded schematic diagram of the air flow and UV exposure path within the UVC chamber.

FIG. 3 illustrates an alternate embodiment assembly 100 having a housing 114 with an inlet opening 47 and an air outlet 147. An LED UVC assembly 31 as previously described directs UVC light into a cylindrical shaped lattice 133. Nodes 42 are suspended within the lattice 133. A filter 35 is located on one end of the assembly and a fan 44 on an opposite end of the assembly. Air 12 is drawn into the inlet 47 of the housing 114 and through the filter 45. The air is drawn by a fan 44 wherein the air passes through the lattice 133, through the fan 44 and out of an air outlet 147 of the housing 114.

Figure 4:
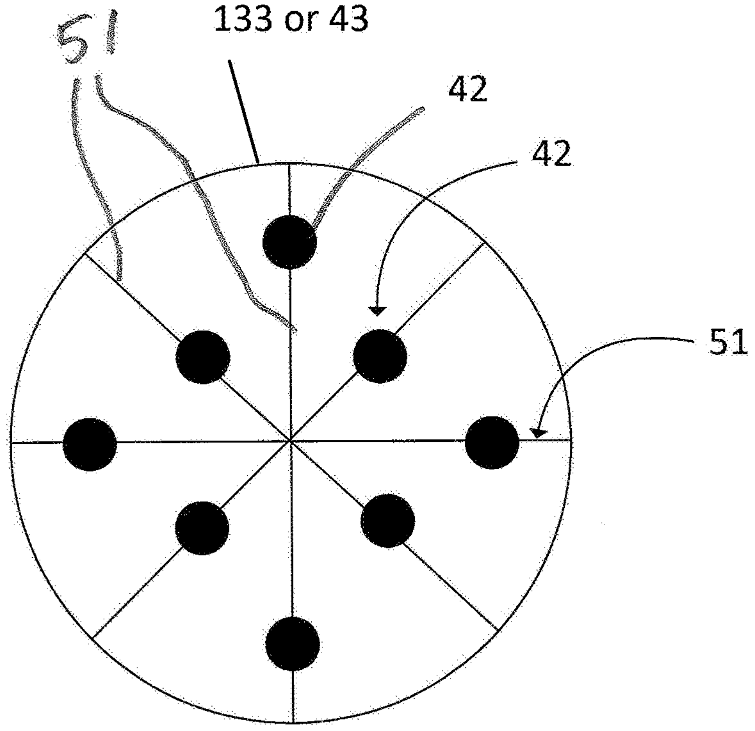
FIG. 4 is schematic sectional diagram taken through plane 4-4 of FIG. 2 and FIG. 3.

The nodes 42 of PTFE are shown in FIG. 4 suspended on diametrical struts 51. The nodes 42 significantly increase the reflectivity within the UVC chamber, ensuring that UVC light is efficiently utilized and redirected to areas that might otherwise receive lower irradiance. The nodes 142 are held on diametrically arranged struts 51 incorporated into the lattice structure 43 or 133.

The strategic placement of PTFE nodes 42 ensures that the UVC light is evenly distributed across the entire $TiO_2$ coated lattice, enhancing the overall photocatalytic reaction efficiency.

PTFE is highly resistant to degradation under UVC radiation, ensuring that the reflective properties of the nodes are maintained over prolonged periods of operation.

By increasing the irradiance and ensuring uniform distribution of UVC light, the PTFE-enhanced lattice structure maximizes the photocatalytic oxidation of pathogens and pollutants.

The integration of PTFE nodes 42 within the 3D-printed $TiO_2$ coated lattice structure 43 or 133 is a novel approach to enhancing the performance of the air purification system. This design not only improves the efficiency of the photocatalytic process but also ensures that the system remains effective and low maintenance over time. The enhanced reflectivity and optimized UVC irradiance provided by the PTFE nodes contribute to a more robust and effective air disinfection and purification system.

These descriptions highlight the innovative use of PTFE nodes to enhance the reflectivity and effectiveness of the UVC chamber, providing a comprehensive view of the system's capabilities and benefits.

The lattice 133 can be dipped into a ceramic slurry and then baked at a low temperature for curing.

For example, the ceramic slurry can be composed of:

- Water;
- Kaolin: 45% kaolin, composed of 25% silica, 10% feldspar, 30% water, 0.3% sodium silicate;
- $TiO_2$: 15 wt % Nanoparticle $TiO_2$;
- Dopants: 0.3 wt % Fe (as $Fe(NO_3)_3$), 1 wt % Ag (as nanoparticles or $AgNO_3$), optional 0.5 wt % Cu (as $Cu(NO_3)_2$); and
- Additives: 0.05 M $H_2O_2$ in reaction medium, optional 0.01 M NaOCl.

This slurry can be refined/can be changed/modified to increase the OH and to tailor to the application.

Use of the slurry can optimize the OH (Hydroxyl radical) by up to 60% from the base $TiO_2$ nanoparticle material.

The embodiments of the invention incorporate a focused optic system designed to create a concentrated beam of UVC energy directed towards the 3D-printed $TiO_2$ coated lattice structure. This system leverages a total internal reflection (TIR) lens 34 to focus UVC light into a high-intensity beam, significantly enhancing both the photocatalytic reaction and UVC disinfection of the air.

The TIR lens is strategically positioned to maximize the focal distance, ensuring that the UVC light travels an optimal distance before reaching the $TiO_2$ coated lattice. This setup allows for a more uniform and intense distribution of UVC energy across the lattice surface, enhancing the depth of UVC penetration into the air stream and improving overall disinfection efficacy.

The focused optic system, through the TIR lens, creates a high-intensity UVC beam that significantly increases the irradiance on the $TiO_2$ coated lattice, enhancing the photocatalytic reaction and the generation of reactive oxygen species (ROS).

The focused UVC beam provides deeper penetration into the air stream, ensuring thorough disinfection of airborne pathogens and pollutants.

The focused optic system can be adjusted to vary the focal length and intensity of the UVC beam, allowing for customization based on specific requirements for air disinfection and purification.

Multiple TIR lenses can be arranged to create a uniform UVC light field across the entire $TiO_2$ coated lattice, ensuring consistent photocatalytic activity and air disinfection.

The high-intensity UVC beam helps maintain the self-cleaning properties of the $TiO_2$ coated lattice by continuously exposing the surface to UVC light, preventing the buildup of organic materials.

The focused UVC beam provides a secondary disinfection mechanism by directly inactivating airborne pathogens, in addition to the photocatalytic oxidation process.

Integrating a focused optic system with a TIR lens 34 into the housing 14 significantly enhances the performance of the air purification system. This approach not only maximizes the photocatalytic efficiency of the $TiO_2$ coated lattice but also ensures a high level of air disinfection through concentrated UVC exposure. The ability to adjust and optimize the UVC beam further enhances the system's versatility and effectiveness in various applications.

The assembly 10 can also include a microprocessor 37 and a power supply 38.

These descriptions emphasize the innovative use of focused optics and TIR lenses to enhance the overall performance of the air purification system, providing comprehensive protection against airborne contaminants.

In the preferred embodiment, the UVC chamber dimensions are optimized for residential and commercial applications. The TIR lens optics are specifically calibrated to ensure even distribution of UVC light across the $TiO_2$-coated surfaces. The air intake system is designed to achieve a balance between air flow rate and exposure time, ensuring thorough disinfection and purification.

Alternative embodiments may include variations in the $TiO_2$ coating thickness, different UVC wavelengths, or additional photocatalytic materials to enhance specific air purification requirements.

SOME ASPECTS OF THE INVENTION

1. An air disinfection and purification system comprises a UVC chamber, wherein the chamber is lined with reflective surfaces and equipped with UVC LEDs emitting at approximately 255 nm-280 nm.
2. The system further comprises a total internal reflection (TIR) lens optic system positioned to direct and focus UVC light within the chamber.
3. The system wherein the interior of the chamber includes a lattice coated with a photocatalytic material comprising titanium dioxide ($TiO_2$).
4. The system wherein the $TiO_2$ coating generates reactive oxygen species (ROS) upon exposure to UVC light, enhancing the disinfection and purification of air.
5. The system further comprises an air intake mechanism designed to control the flow of air through the UVC chamber for optimal exposure to UVC light and the $TiO_2$ surface.
6. The system wherein the UVC chamber is integrated into an existing HVAC system or operates as a standalone unit.
7. The system further comprising sensors and control systems to monitor UVC intensity, airflow, and the condition of the $TiO_2$ coated surface.
8. The system wherein the titanium dioxide ($TiO_2$) coating is formed as a 3D-printed lattice structure to optimize surface area interaction and maximize UV exposure for enhanced air disinfection and photocatalytic oxidation.
9. The system wherein the 3D-printed $TiO_2$ coated lattice structure is designed with a specific pore size and geometry to maximize airflow and ensure thorough exposure to UVC light.
10. The system wherein the $TiO_2$ coated lattice structure is configured to provide a high surface-to-volume ratio, enhancing the photocatalytic reaction efficiency.
11. The system wherein the lattice structure of the $TiO_2$ coated is designed to create turbulent airflow within the UVC chamber, increasing the interaction time between the air and the photocatalytic surfaces.
12. The system wherein the $TiO_2$ coated lattice structure includes a repeating pattern of interconnected nodes and struts to create a robust and stable matrix that withstands prolonged UVC exposure and air flow.
13. The system wherein the $TiO_2$ coated lattice structure is fabricated using a high-precision 3D printing technique to achieve precise control over the structural dimensions and uniform distribution of the $TiO_2$ material.
14. The system wherein the $TiO_2$ coated lattice structure is designed to facilitate easy cleaning and maintenance while maintaining its structural integrity and photocatalytic properties.
15. The system further comprises a method for regenerating the $TiO_2$ coated lattice structure by periodically exposing it to a higher intensity UV light or a specific cleaning solution to maintain its photocatalytic efficiency.
16. The system wherein the $TiO_2$ coated lattice structure is integrated with additional photocatalytic materials to enhance the range of pollutants and pathogens that can be effectively degraded.
17. The system wherein the $TiO_2$ coated lattice structure is modular, allowing for easy replacement or upgrading of the photocatalytic components without disrupting the overall operation of the air purification system.
18. The system wherein the 3D-printed $TiO_2$ coated lattice structure is designed with variable density regions to optimize UV exposure and air flow in different sections of the UVC chamber.
19. The system wherein the $TiO_2$ coated lattice structure is treated with a coating or doped with additional elements to enhance its photocatalytic activity and durability under continuous UV exposure.

20. The system wherein the $TiO_2$ coated lattice structure is designed to be self-supporting, eliminating the need for additional structural components within the UVC chamber and maximizing the volume available for air treatment.
21. The system wherein the 3D-printed $TiO_2$ coated lattice structure includes PTFE (Polytetrafluoroethylene) nodes strategically integrated to enhance reflectivity and optimize the irradiance of UVC energy within the structure.
22. The system wherein the PTFE nodes are positioned to reflect UVC light onto areas of the $TiO_2$ lattice that would otherwise receive less direct exposure, thereby ensuring uniform distribution of UVC energy.
23. The system wherein the PTFE nodes are designed to withstand prolonged exposure to UVC radiation without degrading, maintaining their reflective properties over time.
24. The system wherein the PTFE nodes are integrated into the lattice structure during the 3D printing process to ensure precise placement and optimal alignment with the UVC light sources.
25. The system wherein the PTFE nodes are configured to create multiple reflective pathways for UVC light, increasing the overall irradiance and enhancing the photocatalytic efficiency of the $TiO_2$ coated lattice.
26. The system further comprises a focused optic designed to create a concentrated beam of UVC energy directed towards the $TiO_2$ coated lattice structure to enhance photocatalytic reactions and UVC disinfection.
27. The system wherein the focused optic includes a total internal reflection (TIR) lens that focuses UVC light into a high-intensity beam, increasing the irradiance on the $TiO_2$ coated lattice.
28. The system wherein the TIR lens is positioned to maximize the distance over which UVC light travels, allowing for optimal distribution and penetration of UVC energy through the lattice structure.
29. The system wherein the focused UVC beam created by the TIR lens enhances the depth of UVC penetration into the air stream, improving the disinfection efficacy.
30. The system wherein the focused optic system is adjustable to vary the focal length and intensity of the UVC beam, allowing for customization based on specific air disinfection and purification needs.
31. The system wherein the concentrated UVC beam generated by the focused optic increases the generation of reactive oxygen species (ROS) on the $TiO_2$ surface, enhancing the photocatalytic oxidation of pollutants.
32. The system wherein the focused optic includes multiple TIR lenses arranged to create a uniform and high-intensity UVC light field across the entire $TiO_2$ coated lattice structure.
33. The system wherein the focused UVC beam aids in maintaining the self-cleaning properties of the $TiO_2$ coated lattice by continuously exposing the surface to high-intensity UVC light, preventing buildup of organic materials.
34. The system wherein the focused optic system is integrated with sensors to monitor and adjust the UVC beam intensity and focus in real-time, ensuring consistent and optimal performance.
35. The system wherein the focused UVC beam created by the TIR lens not only enhances the photocatalytic reaction but also provides a secondary disinfection mechanism by directly inactivating airborne pathogens.

From the foregoing, it will be observed that numerous variations and modifications may be effectuated without departing from the spirit and scope of the invention. It is to be understood that no limitation with respect to the specific apparatus illustrated herein is intended or should be inferred.

The invention claimed is:

1. An air disinfection and purification system, comprising:
a housing; and
a treatment assembly enclosed by the housing, wherein:
the treatment assembly includes ultraviolet-C LED units;
the treatment assembly includes a 3D-printed lattice coated with a thin layer of titanium dioxide ($TiO_2$);
the 3D-printed lattice includes interconnected nodes and struts; and
the nodes comprise polytetrafluoroethylene suspended on the struts.

2. The air disinfection and purification system according to claim 1, wherein the housing includes one or more air intakes and one or more air outlets for a controlled flow of air through the housing.

3. The air disinfection and purification system according to claim 2, wherein the one or more air intakes include an air intake at each opposite end of the housing.

4. The air disinfection and purification system according to claim 3, wherein a filter and a fan are arranged between one intake of the one or more air intakes and the 3D-printed lattice within the housing.

5. The air disinfection and purification system according to claim 4, wherein the housing comprises baffles for the controlled flow of air to pass through a chamber defined by the housing.

6. The air disinfection and purification system according to claim 4, wherein the 3D-printed lattice is designed with variable density regions to optimize UV exposure and air flow in different areas of a chamber defined by the housing.

7. The air disinfection and purification system according to claim 4, wherein the 3D-printed lattice is treated with a coating or doped with additional elements to enhance its photocatalytic activity and durability under continuous UV exposure.

8. The air disinfection and purification system according to claim 4, wherein the polytetrafluoroethylene balls are positioned to reflect ultraviolet-C light onto areas of the 3D-printed lattice that would otherwise receive less direct exposure, thereby ensuring uniform distribution of ultraviolet-C energy.

9. The air disinfection and purification system according to claim 4, further comprising a focused optic including multiple TIR (total internal reflection) lenses arranged to create a uniform and high-intensity ultraviolet-C light field across the entire 3D-printed lattice.

10. The air disinfection and purification system according to claim 5, wherein the housing and the 3D-printed lattice are cylindrical and the baffles are annular.

11. The air disinfection and purification system according to claim 1, wherein the nodes are integrated into the 3D-printed lattice positioned to reflect ultraviolet-C light onto less directly exposed areas of the 3D-printed lattice.

12. The air disinfection and purification system according to claim 4, wherein the housing is cylindrical and the one or more air intakes comprises one air intake at a first end of the housing and the one or more air outlets includes one outlet arranged at a second end of the housing opposite to the first end.

13. The air disinfection and purification system according to claim 1, wherein the struts are diametrically arranged within the treatment assembly.

14. The air disinfection and purification system according to claim 4, wherein the ultraviolet-C LED units emit at a wavelength of 255 nm-280 nm.

15. The air disinfection and purification system according to claim 4, wherein the ultraviolet-C LED units each include an ultraviolet-C LED emitter and a TIR lens optic system positioned to direct and focus ultraviolet-C light efficiently.

16. The air disinfection and purification system according to claim 4, further comprising a microprocessor and a power supply comprising sensors and control systems to monitor ultraviolet-C intensity, airflow, and the condition of the thin layer of $TiO_2$.

17. The air disinfection and purification system according to claim 1, wherein the housing comprises reflective inner surfaces.

* * * * *